US012576207B2

(12) United States Patent
Krey et al.

(10) Patent No.: US 12,576,207 B2
(45) Date of Patent: Mar. 17, 2026

(54) COMPUTER-IMPLEMENTED DIABETES MANAGEMENT METHODS

(71) Applicant: Roche Diabetes Care, Inc., Indianapolis, IN (US)

(72) Inventors: David Christopher Krey, Heidelberg (DE); Hans-Juergen Kuhr, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 849 days.

(21) Appl. No.: 17/851,679

(22) Filed: Jun. 28, 2022

(65) Prior Publication Data

US 2022/0323676 A1    Oct. 13, 2022

Related U.S. Application Data

(63) Continuation of application No. PCT/US2020/066746, filed on Dec. 23, 2020.

(Continued)

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01); *A61M 5/14244* (2013.01); *A61M 2005/14208* (2013.01); *A61M 2005/1726* (2013.01); *A61M 2205/502* (2013.01); *A61M 2205/52* (2013.01)

(58) Field of Classification Search
CPC ............ A61M 5/1723; A61M 5/14244; A61M 2005/14208; A61M 2005/1726; A61M 2205/502; A61M 2205/52; A61B 5/14532; A61B 5/4839

See application file for complete search history.

(56) References Cited

U.S. PATENT DOCUMENTS 8,734,422 B2 *    5/2014    Hayter ............... A61B 5/14532
                                                    702/19
9,594,354 B1    3/2017    Kahn et al.
(Continued)

FOREIGN PATENT DOCUMENTS

WO    WO-2011041007 A1 *    4/2011    ......... A61B 5/14532
WO    WO-2013023014 A1 *    2/2013    ........ A61M 5/14244
(Continued)

OTHER PUBLICATIONS

International Search Report and Written Opinion; PCT/US2020/066746; May 11, 2021; pp. 1-13.

*Primary Examiner* — Cris L. Rodriguez

(57) ABSTRACT

A computer-implemented diabetes management method includes a first determination of an insulin bolus related to one or more obtained glucose values and optionally the expected carbohydrate content of a meal to be ingested, a re-calculation of an insulin bolus in consideration of a user's body parameter information as measured by a body-worn sensor, providing a notification to the user if there is a significant deviation between the two calculated bolus amounts, and a user input whether the calculated insulin bolus or the re-calculated insulin bolus is selected by the user for bolus administration.

12 Claims, 4 Drawing Sheets

Related U.S. Application Data

(60) Provisional application No. 62/955,338, filed on Dec. 30, 2019.

(51) Int. Cl.
*A61B 5/145* (2006.01)
*A61M 5/142* (2006.01)

(56) References Cited

U.S. PATENT DOCUMENTS

| | | | | |
|---|---|---|---|---|
| 10,251,583 | B2 * | 4/2019 | Bernini | A61B 5/7275 |
| 10,458,973 | B2 * | 10/2019 | Galley | G01N 33/48792 |
| 2009/0006061 | A1 * | 1/2009 | Thukral | G16H 50/20 |
| | | | | 703/11 |
| 2009/0006129 | A1 * | 1/2009 | Thukral | G16H 20/10 |
| | | | | 705/2 |
| 2009/0069787 | A1 | 3/2009 | Estes | |
| 2011/0071464 | A1 * | 3/2011 | Palerm | A61M 5/1723 |
| | | | | 604/66 |
| 2011/0137141 | A1 * | 6/2011 | Razoumov | A61B 5/0002 |
| | | | | 600/324 |
| 2014/0066884 | A1 * | 3/2014 | Keenan | A61B 5/14503 |
| | | | | 604/504 |
| 2015/0217053 | A1 * | 8/2015 | Booth | A61B 5/14532 |
| | | | | 604/504 |
| 2018/0296757 | A1 * | 10/2018 | Finan | G16H 20/17 |
| 2022/0352099 | A1 * | 11/2022 | Albright | G06F 21/86 |

FOREIGN PATENT DOCUMENTS

| | | | |
|---|---|---|---|
| WO | 2015116371 | A1 | 8/2015 |
| WO | 2018194838 | A1 | 10/2018 |
| WO | 2019025506 | A1 | 2/2019 |

* cited by examiner

COMPUTER-IMPLEMENTED DIABETES MANAGEMENT METHODS

CLAIM OF PRIORITY

This application claims the benefit of International Application No. PCT/US2020/066746, which is entitled "COMPUTER-IMPLEMENTED DIABETES MANAGEMENT METHODS," and was filed on 23 Dec. 2020, the entire contents of which are incorporated herein by reference. This application claims the further benefit of U.S. Provisional Application No. 62/955,338, which is entitled "COMPUTER-IMPLEMENTED DIABETES MANAGEMENT METHODS," and was filed on 30 Dec. 2019, the entire contents of which are incorporated herein by reference.

FIELD

The present disclosure relates to bolus calculation methods and the management of therapeutic fluid infusion in general. More particularly, this application concerns methods and devices relating to the use of a bolus calculator for calculating a bolus dose of therapeutic fluid.

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep glucose levels at an optimum level. Healthcare may often include both establishing a therapeutic program and monitoring the progress of the afflicted person. Monitoring blood glucose levels is an important process that is used to help diabetics maintain blood glucose levels as near to normal as possible throughout the day. Monitoring can also allow successful treatment of a diabetic by altering therapy as necessary. Monitoring may allow the diabetic to follow more closely his or her condition and, in addition, can provide information of value to the healthcare provider in determining both progress of the patient and detecting any need to change the patient's therapy program.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a noncontinuous system may require a diabetic to apply a blood sample to a reagent-impregnated region of a test strip, and determine a blood glucose level by an electrochemical analysis method or comparing the color of the reagent-impregnated regions of the test strip with a color chart supplied by the test strip manufacturer. Alternatively, many patients use a continuous glucose monitoring (CGM) device to monitor their glucose level on an ongoing basis. In order to perform CGM, a glucose sensor may be placed under the skin such that the sensor is capable of measuring the glucose level of the person in the interstitial fluid. The glucose sensor may periodically measure the glucose level of the person and transmit the glucose measurement results at a known time interval, such as every minute, to an electronic monitor. Individuals with diabetes are currently using CGM to calculate correction boluses using the same equations designed for self-monitoring of blood glucose levels. This can increase the risk of hypoglycemia due to the increased uncertainty of CGM.

Persons with diabetes often carry specialized electronic meters, called blood glucose meters, which allow them to periodically measure their glucose levels and assist them in taking appropriate action, such as administering insulin or ingesting carbohydrates. Some diabetics may also wear a CGM device to manage their diabetes. These CGM devices generally provide continuous glucose data values which can provide for better control of a user's blood glucose values. These persons may also carry with them a portable communication device, such as a mobile phone, a personal digital assistant, a tablet or similar device which communicates with their blood glucose meter or CGM.

Smart hearing aids, which comprise one or more sensors to collect information about a wearer's activity or health status, are known. These hearing aids are often integrated into a communication network. Hearing aids can be used to draw a wearer's attention to a status of devices of the network by playing an audio message.

In the future, more body sensors will be available to persons with diabetes where the body sensors will provide for collecting information other than blood glucose values. Since these sensors are not necessarily part of a proprietary diabetes management solution provided by a single manufacturer or company, their integration into a more capable diabetes management system may increase certain risks for the users. Minimizing these risks is one goal of the embodiments disclosed herein.

The information above recites background information related to the present disclosure and is not necessarily an admission of certain teachings as prior art.

SUMMARY

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Embodiments described herein provide for safer methods for calculating insulin boluses, typically meal boluses and correction boluses. Embodiments disclosed herein detail calculations using an algorithm that improves the accuracy of bolus calculations by accounting for activity or health status of the user.

There exists a need in the art for diabetes management methods and systems that will provide two (or more) suggestions for a bolus, such that a patient can select the bolus which suits his/her needs best. These methods provide a patient with an alternative bolus suggestion, which is determined by taking into account additional information concerning the patient's current activity or health status. The additional information may be achieved by use of a body-worn sensor. The body-worn sensor could be arranged/integrated in a hearing aid and/or could be arranged/integrated in a smart watch, such as an Apple Watch for example, or arranged/integrated in an activity tracker, such as a Fitbit device.

Persons with diabetes often carry a handheld glucose meter as well as a portable computing device, such as a mobile phone. Given the close proximity of these two devices, the portable computing device can serve as a data collector for the glucose measurements taken by the glucose meter.

In particular, in an embodiment, a computer-implemented diabetes management method for determining an insulin bolus by a diabetes management device or component thereof comprising a processor is disclosed herein, and the method comprises:

receiving by the processor, a glucose value;

calculating by the processor a first calculated insulin bolus based on the received glucose value;

receiving by the processor body parameter information from at least one body-worn sensor device;

determining by the processor a re-calculated insulin bolus based on the body parameter information;

notifying by a first user interface the user if there is a significant deviation between the amount of the first determined insulin bolus and the amount of the re-calculated insulin bolus; and receiving by the first user interface or by a second user interface within a given timeframe a user input whether the calculated insulin bolus or the re-calculated insulin bolus is selected for bolus administration.

In an embodiment, in the first receiving step, the processor receives the glucose value from a glucose monitoring device.

In one embodiment, the method includes administering the selected bolus amount.

In an embodiment, the method includes determining by the processor a final insulin bolus if no user input was received within the given timeframe, wherein the final insulin bolus is the lesser value of either the first calculated insulin bolus or the re-calculated insulin bolus. In another embodiment, the method calls for setting the final insulin bolus as the first calculated insulin bolus.

The method of any one of the previous embodiments can include steps wherein the processor receives information about a carbohydrate content associated with a meal which is to be ingested prior to determining the first determined insulin bolus, and wherein the carbohydrate content is considered by the processor in determining the first determined insulin bolus.

The method of any one of the previous embodiments can include use of a body-worn sensor device which comprises a hearing aid, a smart watch, or an activity tracker, or any combination thereof.

The method of any one of the previous embodiments can include use of body parameter information that includes at least one of the user's heart beat rate, internal body temperature, respiratory rate, speed of movement or acceleration of movement.

In the method of any one of the previous embodiments, the notification can include providing an audible alarm or warning to the user by use of a hearing aid, a smart watch, or an activity tracker, or any combination thereof.

Embodiments described herein provide for a method for integrating additional sensor information into a diabetes management system wherein the additional sensor(s) may be provided by different manufacturers and/or companies. The method provides for calculating via the algorithm a standard insulin bolus dose typically utilizing an insulin sensitivity factor of a user and a pre-set target glucose level. In an embodiment, a risk of hypoglycemia can be minimized by automatically selecting the minimum value between the first calculated insulin bolus dose and the re-calculated insulin bolus dose if there is no user response within a given period of time. There is thus provided in selected embodiments a way to reduce the risk to patients in using the system in situations where the first calculated bolus deviates significantly (typically above a preset threshold) from the second calculated bolus.

Additional embodiments described herein provide for a system or method for determining an insulin amount, the system or method comprising a processor, wherein the processor is configured to:

receive continuous glucose value information from a continuous glucose monitoring device;

process the received glucose information by utilizing a loop algorithm to calculate the insulin needed to keep the user within a given glucose value range;

receive body parameter information based on at least one body-worn sensor that monitors at least one body parameter;

re-calculate the insulin needed to keep the user within the given glucose value range based on the body parameter information;

provide a notification to the user if the re-calculation of insulin needed leads to a determination that the user is running out of the given glucose value range within a preselected period of time;

receive an input by the user during a preset period of time whether the body parameter information shall be accepted for use by the loop algorithm; and in case of no response by the user within the preset period of time, determine that the system shall administer the lower insulin amount which was calculated by the loop algorithm with and without consideration of the body parameter information.

In another embodiment, the previous system or method can be configured such that the processor determines that the system shall administer the insulin amount calculated without consideration of the body parameter information.

In the previous two embodiments of the system or method, the body-worn sensor device comprises a hearing aid, a smart watch, or an activity tracker, or a combination thereof.

In the previous embodiments of the system or method, the body parameter information includes at least one of the user's heart beat rate, internal body temperature, respiratory rate, speed of movement or acceleration of movement.

In the previous embodiments of the system or method, the processor is configured to conduct the notification by communicating to a hearing aid, a smart watch, or an activity tracker, or any combination thereof to provide an audible alert to the user.

DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

Figure 3:
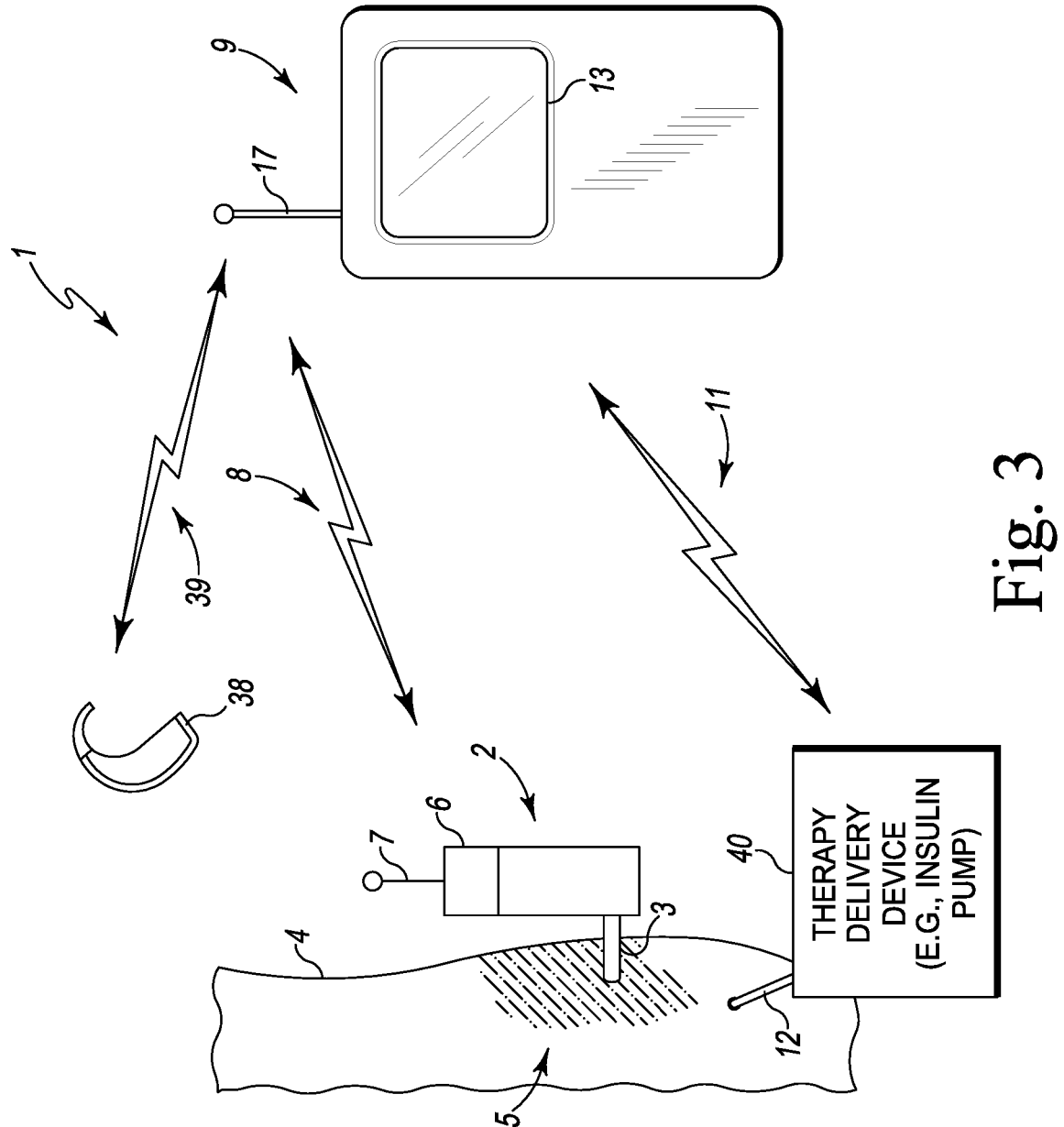
Figure 4:
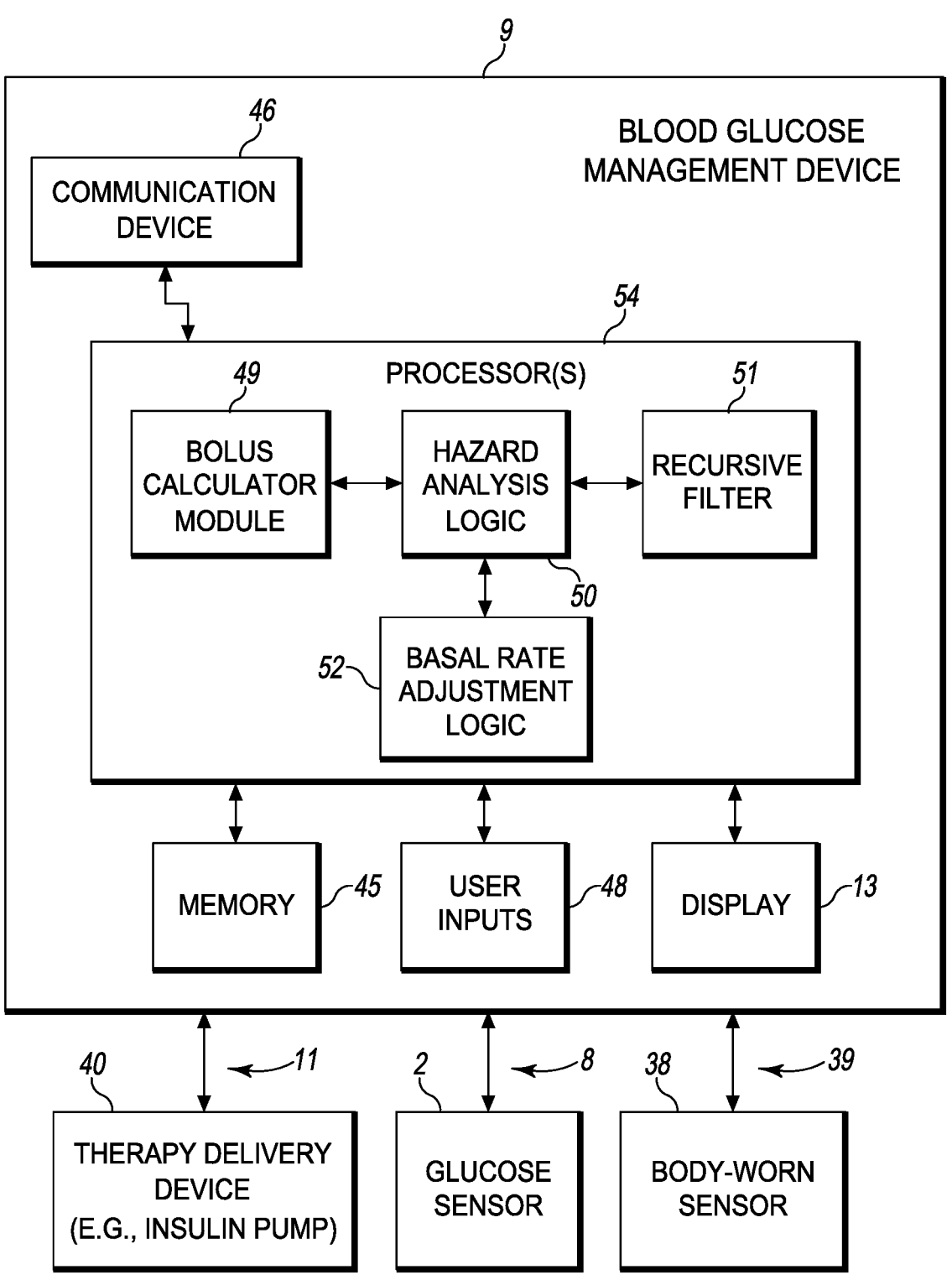

FIG. 3 illustrates a CGM system embodiment including a body-worn sensor device in bidirectional wireless communication with other components of the CGM system according to one or more embodiments described herein; and FIG. 4 illustrates an exemplary blood glucose management device, therapy delivery device, glucose sensor, and body-worn sensor device of the CGM system of FIG. 3, the blood glucose management device including a bolus calculator module, hazard analysis logic, a basal rate adjustment logic, and a recursive filter.

DETAILED DESCRIPTION

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Parts of methods described herein such as mathematical determinations, calculations, inputting of data for computations or determinations of equations or parts thereof can be performed on parts of or one or more computers or computer systems that can include one or more processors, as well as software to run or execute programs and run calculations or computations.

Methods and systems and parts thereof described herein can be combined to implement embodiments of the invention. Forms of words used herein can have variations: for example when a word such as "calculate" is used, this implies that variations such as "calculated" and "calculating" are understood and have been considered.

As used herein, "user," "patient," and "person" are used to refer to an individual interacting with the disclosed diabetes management systems to improve that individual's health via the improvements described herein.

Figure 1:
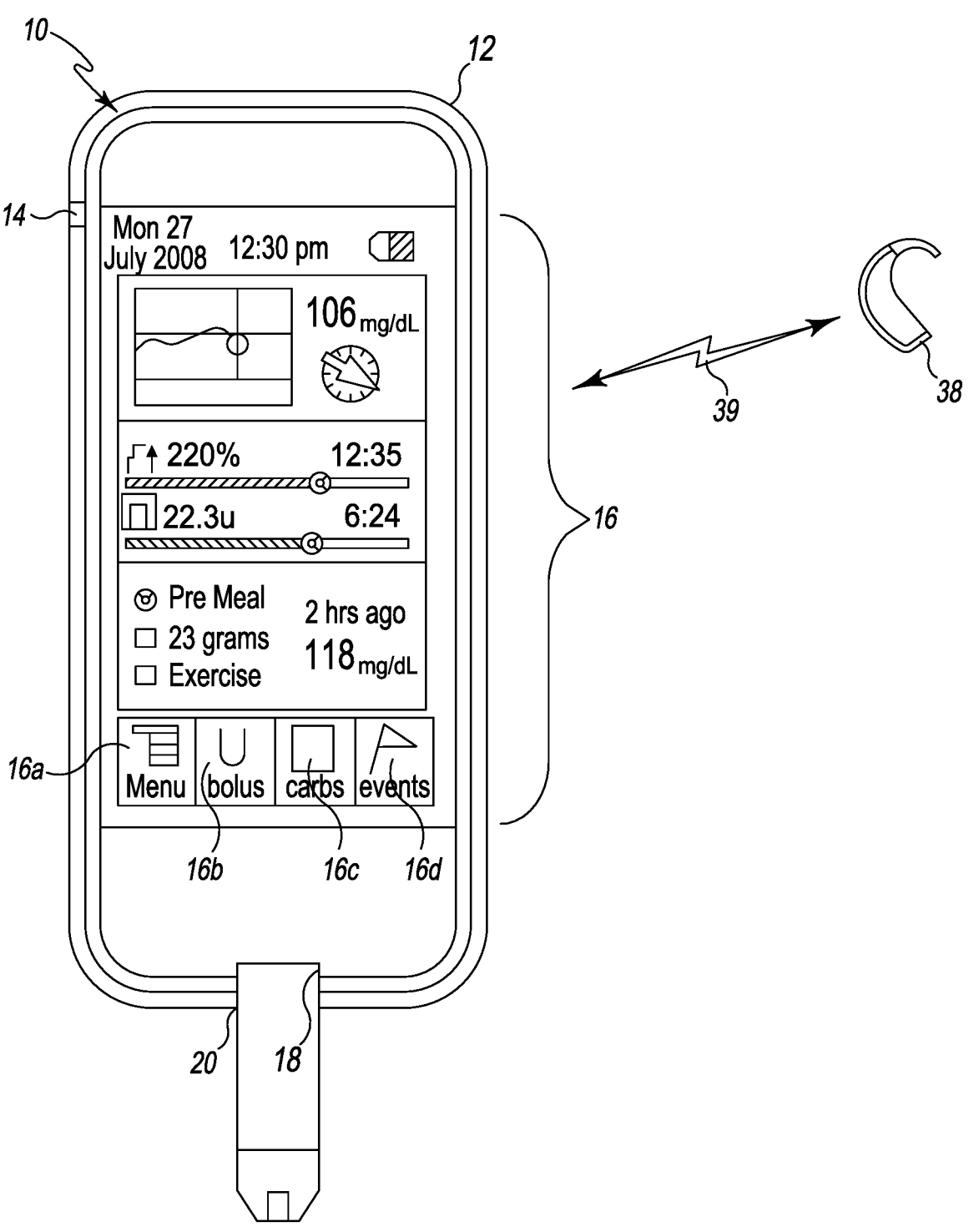
FIG. 1 is a diagram depicting a handheld glucose meter which is configured to be in data communication with a diabetes management application residing on a mobile phone and also depicting a body-worn sensor device in bidirectional wireless communication with the glucose meter.

Referring to FIG. 1, there is shown a high-level drawing of one embodiment of a handheld diabetes management device 10 that may be used in measuring the blood glucose (bG) of a patient and implementing a bolus calculation or carbohydrate suggestion. Typically, the device 10 includes a housing 12 that may contain user unit control switches 14 (e.g., ON/OFF), a touchscreen display 16, and a port 18 into which a bG test strip 20 may be inserted. The display 16 may display user selectable options for allowing the user to access a software driven menu 16a of various selections, a selection 16b for allowing the user to enter bolus information, a selection 16c for enabling the user to enter carbohydrate information for snacks or meals, and a selection 16d for allowing the user to enter information pertaining to health events (e.g., meals, exercise, periods of stress, periodic physiological events such as a menstrual cycle, etc.) that may affect the user's bG measurement being read by the device 10. Although the display 16 will be described herein as a touchscreen display, it will be appreciated that any other suitable form of display may be incorporated (e.g., LED, etc.). If a touchscreen display is not used, the user control switches 14 may need to include specific buttons or controls by which the user is able to select various options and input markers needed to carry out the bolus calculation or carbohydrate suggestion. It will be appreciated that the above is a high-level description of the device 10, and in practice, the device may include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
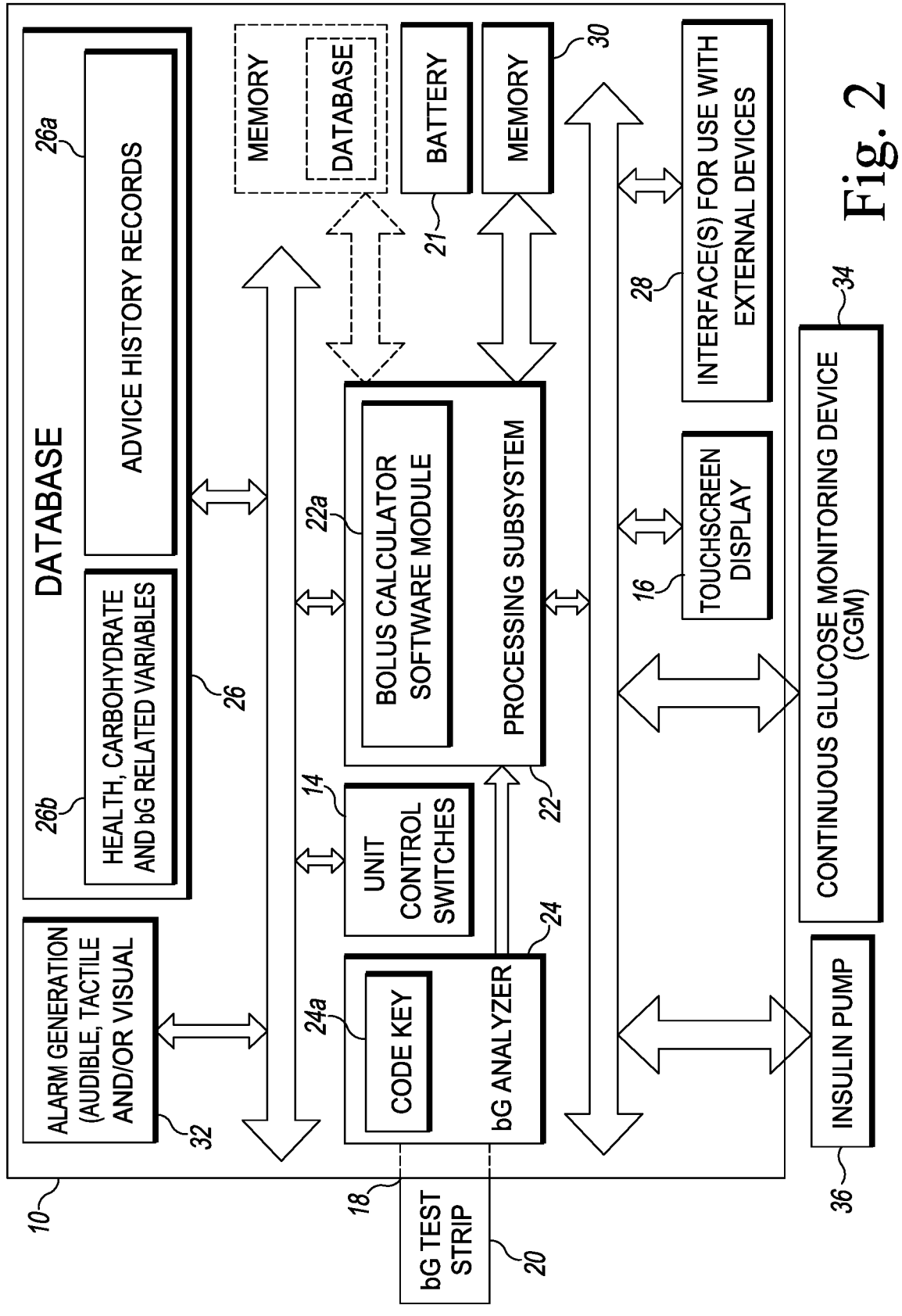
FIG. 2 is a block diagram of an exemplary hardware arrangement for the glucose meter.

Referring to FIG. 2, a high-level block diagram of the device 10 is shown. The device 10 can include a rechargeable or non-rechargeable battery 21 for powering the various electronic components of the device 10. A processing subsystem 22 (e.g., a microprocessor based subsystem) is included that receives information from a bG analyzer 24. The bG analyzer 24 can be located adjacent the port 18 of the housing 12 to permit the bG analyzer 24 to read the bG test strip 20. The bG analyzer 24 can include a code key 24a that includes calibration information for the bG test strip 20 being read. The processing subsystem 22 can also be in communication with a database 26 that is used to store bG test values obtained from the bG analyzer 24 and other important health related information for the user. In particular, the database 26 can include a subsection 26a for storing recommended bolus and carbohydrate advice history records (hereinafter "advice history records") that are still active in their influence of current and future advice as well as historical records, and a section 26b for storing medication (insulin), health, carbohydrate and bG related variables (e.g., insulin sensitivities of the user for various time segments of the day) pertinent to the user. It will be appreciated that the database 26 will typically be formed by a non-volatile memory. Further, the bG related variables such as the insulin sensitivities of the user can be stored as global parameters and may not be in the advice history records.

The processing subsystem 22 can also be in communication with the display 16, the user control switches 14, and one or more interfaces 28 for interfacing the device 10 to other external devices. The processing subsystem 22 can also be in communication with a memory (such as a RAM) 30 for storing various types of information (e.g., meal and bed times) that are input by the user, as well as any other information requiring temporary or permanent storage. However, it will be appreciated that the database 26 and the memory 30 could be implemented in a single memory device (e.g., RAM) if desired, as indicated in phantom in FIG. 2. The processing subsystem 22 can be in communication with an alarm generation subsystem 32 that is used to generate an alarm or warning comprising audible signals, tactile signals (e.g., a vibration signal) or possibly even visual signals serving as warnings or alarms such as illuminated lights (e.g., LEDs) on the device 10. In one embodiment, the processing subsystem 22 can also receive inputs from a remote continuous glucose monitoring ("CGM") device 34 secured to the user's body such that device 10 is continually updated with glucose information for the user. Finally, in one embodiment, the processing subsystem 22 can be in communication with a remote insulin infusion pump 36 (herein referred to as an "insulin pump 36") worn by the user so that the device 10 is able to communicate bolus information to the insulin pump 36. By "remote" it is meant that the CGM device 34 and the insulin pump 36 are each located outside of the device 10 but otherwise still in communication with the device 10. It should be appreciated that the device 10 can communicate with the insulin pump 36 either through a wired or wireless connection.

The device 10 can be used to implement a non-transitory machine-readable code, for example a diabetes management application comprising a bolus calculator software module 22a (herein referred to as "bolus calculator 22a"), that is run by the processing subsystem 22 which includes a processor. The bolus calculator 22a can be formed as a single module or as a collection of independent modules that run concurrently on the processing subsystem 22. The processing subsystem 22, working in connection with the bolus calculator 22a, receives a wide variety of user inputs applied by the user through the touchscreen display 16 to generate a recommended correction bolus, a recommended meal bolus, a recommended total bolus, or when appropriate a suggested carbohydrate amount. The suggested carbohydrate amount may be provided in response to the detection by the device 10 of a hypoglycemic bG test value. The operations and capabilities of the device 10 will be explained in detail in the following paragraphs. The device 10 significantly enhances the convenience and ease of use to the user through the implementation of a plurality of customizable inputs that enable the user to program the device 10 with unique health information pertinent to the user. More specifically, the device 10 allows the user to program the device 10 with health information which even more completely enables the device 10 to take into account unique health conditions affecting the user, as well as regular occurring and non-regular occurring health events that could otherwise have an impact on the bolus and carbohydrate calculations made by the device 10.

The diabetes management application may receive one or more glucose measurements and a measurement time associated with each of the one or more glucose measurements. The diabetes management application determines a bolus calculation based on the one or more glucose measurements. Further teachings relating to bolus calculators which would be suitable for purposes of the present invention can be found in U.S. Pat. No. 6,925,393 B1, issued Aug. 2, 2005, and U.S. Pat. No. 9,786,024 B2, issued Oct. 10, 2017, the entire disclosures of each of which are hereby incorporated by reference.

The diabetes management application may generate a bolus recommendation based on a bolus calculation. For example only, the bolus recommendation may include instructing the patient to take an amount of insulin or to consume carbohydrates in order to increase or decrease the patient's blood glucose. In order for the diabetes management application to provide an effective bolus recommendation, the bolus recommendation must occur within a predetermined period following the timestamp of the blood glucose measurement. For example, the predetermined period may be less than 10 minutes. The diabetes management application determines whether the timestamp is within the predetermined period.

The diabetes management application may generate a request for information input screen. The request for information input screen can include a display of previously received data. For example, the request for information input screen may display a previously recorded glucose measurement. The request for information input screen advises the patient to input specified information. For example, the specified information may include meal information, and the total number of carbohydrates the patient has consumed or will consume.

The diabetes management application determines a bolus calculation based on the one or more glucose measurements received from the meter 12 and manually recorded patient data, such as insulin values and meal information. The diabetes management application generates the bolus recommendation based on the bolus calculation. The diabetes management application also generates an alternative or re-calculated bolus recommendation which is based on (i.e., takes into account) body parameter information indicating the patient's activity or health status as further described elsewhere herein. Such activity or health status information is provided by a body-worn sensor, one example of which is a hearing aid 38 (see FIG. 1) that includes a sensor such as a sensor that measures the wearer's internal body temperature by measuring the same within the wearer's ear. The hearing aid would typically communicate such activity or health status information with the glucose meter 12 using bidirectional wireless communication as shown in FIG. 1 via communication link 39.

Referring to FIG. 3, in one embodiment, an exemplary CGM system 1 is illustrated for monitoring the glucose level of a person having diabetes. In particular, the CGM system 1 is operative to collect and/or transmit measured glucose values at a predetermined, adjustable interval, such as every one minute, five minutes, or at other suitable intervals. The CGM system 1 illustratively includes a glucose sensor 2 having a sensor, needle or probe 3 that is inserted under a skin surface 4 of the person. The end of the needle 3 is positioned in a region containing an interstitial fluid 5 such that measurements taken by the glucose sensor 2 are based on the level of glucose in the interstitial fluid 5. The needle can also be placed in a region with blood and/or other bodily fluid. The glucose sensor 2 is positioned adjacent the abdomen of the person or at another suitable location. The glucose sensor 2 may comprise other components as well, including but not limited to a wireless transmitter 6 and an antenna 7. Note that the glucose sensor 2 is not drawn to scale and may in certain embodiments be mounted generally as a puck on the skin surface. The glucose sensor 2 may alternatively use other suitable devices for taking measurements, such as, for example, a non-invasive device (e.g., an infrared light sensor). Upon taking a measurement, the glucose sensor 2 transmits the measured glucose value(s) via a communication link 8 to a computing device 9 (also sometimes referred to as management device 9), illustratively a blood glucose management device 9, a smart phone 9 or a bolus calculator 9 (in specific embodiments the computing device 9 has a housing, as described herein, and is a stand-alone device, working in conjunction with a processor(s) which includes a bolus calculator module performing logic properties of, for example, the computing device).

In some embodiments, the CGM system 1 can further include a therapy delivery device 40, illustratively an insulin infusion pump 40, for delivering therapy (e.g., insulin) to the person. The pump 40 can have a single housing or can have a two-part housing where one part is reusable and the other disposable, where the disposable part can include a power source such as a battery. The insulin pump 40 is in communication with the management device 9 via a bidirectional communication link 11, and the management device 9 is able to communicate bolus and basal rate information to the insulin pump 40. The insulin pump 40 can include a cannula or catheter 12 having a needle that is inserted through the skin 4 of the person for infusing insulin. Insulin pump 40 is illustratively positioned adjacent the abdomen of the person or at another suitable location. Similar to the glucose sensor 2, the infusion pump 40 also typically includes a wireless transmitter and an antenna for communication with management device 9. The insulin pump 40 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from the management device 9. Similarly, the basal rate of the basal insulin is set based on user input or in response to a command from management device 9. Infusion pump 40 may optionally include a display for displaying pump data and a user interface providing user controls. In an alternative embodiment, insulin pump 40 and the glucose sensor 2 may be provided as a single device worn by the patient, and at least a portion of logic run by a processor may reside on this single device. Bolus insulin may also be injected by other means, such as manually by the user via an insulin pen or a needle.

Similar to the embodiment shown and described earlier, the CGM system includes an additional body-worn sensor. One embodiment of such a body-worn sensor is the hearing aid 38 which can communicate body parameter information such as the above-referenced activity or health status information with the management device 9 via the communication link 39 and optionally communicating in a bidirectional wireless manner.

Referring to FIGS. 3 and 4, communication links 8, 11 and 39 are illustratively wireless, such as a radio frequency ("RF") or other suitable wireless frequency, in which data and controls are transmitted via electromagnetic waves between the sensor 2, the therapy delivery device 40, the body-worn sensor 38, and the management device 9. Bluetooth® is one exemplary type of wireless RF communication system that can use a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 8, 11 and 39 may facilitate communication between multiple devices, such as between the glucose sensor 2, the management device 9, the insulin pump 40, the body-worn sensor 38, and other suitable devices or systems. In another embodiment, the glucose sensor 2 could communicate with the management device 9 via communicating with the insulin pump 40. Wired links may alternatively be provided between devices of the system 1, such as, for example, a wired Ethernet link. Other suitable public or proprietary wired or wireless links may also be used.

FIG. 4 illustrates an exemplary embodiment of the management device 9 of the CGM system 1 of FIG. 3. The management device 9 includes at least one processing device 54 that executes software and/or firmware code stored in a memory 45 of management device 9. The software/firmware code contains instructions that, when executed by the processor 54 of the management device 9, causes the management device 9 to perform the functions described herein. The management device 9 may alternatively include one or more application-specific integrated circuits (ASICs), field-programmable gate arrays (FPGAs), digital signal processors (DSPs), hardwired logic, or combinations thereof. While the management device 9 is illustratively a glucose monitor 9, other suitable management devices 9 may be provided, such as, for example, desktop computers, laptop computers, computer servers, personal data assistants ("FDA"), smart phones, cellular devices, tablet computers, infusion pumps, an integrated device including a glucose measurement engine and a PDA or cell phone, etc. Although the management device 9 is illustrated as a single management device 9, multiple computing devices may be used together to perform the functions of the management device 9 described herein. FIG. 4 also illustrates that the system can include a bolus calculator module 49, a hazard analysis logic component 50 (such as for accounting for time/rates of change of glucose levels in calculations), a recursive filter 51 (such as for removing noise in calculations or adjusting for the probability of glucose sensor accuracy), and/or a basal rate adjustment logic component 52 (such as for adjusting for the effect of the user activities on rates in calculations).

The memory 45 is any suitable computer readable medium that is accessible by the processor 54. The memory 45 may be a single storage device or multiple storage devices, may be located internally or externally to the management device 9, and may include both volatile and non-volatile media. Further, the memory 45 may include one or both of removable and non-removable media. Exemplary memory 45 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the management device 9.

The management device 9 further includes a communication device 46 operatively coupled to processor 54. The communication device 46 includes any suitable wireless and/or wired communication module operative to transmit and receive data and controls over the communication links 8, 11 and 39 between the device 9, the glucose sensor 2, the body-worn sensor 38, and the insulin pump 40. In one embodiment, the communication device 46 includes an antenna 17 (FIG. 3) for receiving and/or transmitting data wirelessly over the communication links 8, 11 and 39. The management device 9 stores in the memory 45 measured glucose results and other data received from the glucose sensor 2, the body-worn sensor 38, and/or the insulin pump 40 via the communication device 46.

The management device 9 includes one or more user input devices 48 for receiving user input. The input devices 48 may include pushbuttons, switches, a mouse pointer, keyboard, touch screen, or any other suitable input device. The display 13 is operatively coupled to the processor 54. The display 13 may comprise any suitable display or monitor technology (e.g., liquid crystal display, etc.) configured to display information provided by the processor 54 to the user. Processor 54 is configured to transmit to the display 13 information related to the basal rate and bolus information. Moreover, the displayed information may include warnings and/or alarms, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as from about 50 to about 70 mg/dL of glucose in blood. Management device 9 may also be configured to communicate information or warnings to the person via a sense of touch, for example, by vibrating, or by sending information or warnings to the body-worn sensor (such as the hearing aid 38) for the body-worn sensor to provide the information or warnings to the user.

For a further description of additional features that may be provided by the bolus calculator module, see U.S. Pat. Nos. 10,458,973 B2 and 10,251,583 B2, the entire disclosures of which are incorporated by reference herein.

In specific embodiments, methods comprise removing the corresponding meal bolus when the selected insulin dose is negative. Methods can also include a carbohydrate suggestion when the selected insulin dose is negative.

Methods and devices described herein can be used instead of or with a system in conjunction with methods described in U.S. Patent Application Publication No. 2016/0287184 A1, which is hereby incorporated by reference in its entirety.

Specific embodiments herein comprise an alarm or warning, sometimes referred to as an alert. More specifically, the alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert.

In one example, an event or a pattern can trigger an alarm or warning, or a combination of the two (i.e., an alert) that can be used to alert the patient to take specific actions whenever a particular event occurs. For example, the pattern can be a post-prandial event, hypoglycemic event, exercise, meals, etc. or any other problematic event or pattern that has occurred in the patient's past physiological data. Thus, when the event is detected again on a real-time basis, the system 1 will alert the patient to that fact such as via the display 13 and/or vibration and/or noise. The bolus calculator can have the processor 54 or multiple processors 54 (including the bolus calculator module 49) interacting with various hardware and/or software to send the alert to a clinician if the person's glucose level falls below (or is predicted to fall below) a predetermined hypoglycemic threshold; an alert can also be sent if the measure of uncertainty is above a certain point. The bolus calculator can be configured to transmit the alert wirelessly and activate an application on the clinician's computer when the computer comes online and/or is otherwise turned on/activated.

In an embodiment, the first determined insulin bolus related to the received blood glucose value is calculated by utilizing one of the traditional bolus calculators described above.

In one embodiment, the diabetes management application can determine whether no user input is received in the given timeframe, and if so, can instruct a connected insulin therapy device to administer to the patient the lesser value of either the first calculated insulin bolus or the re-calculated insulin bolus. In another embodiment, if no such user input is received in the given timeframe, the system can utilize the first calculated insulin bolus as the amount to be administered to the patient or the system can be configurable by the patient to utilize either the first calculated insulin bolus or the re-calculated insulin bolus.

Regarding the re-calculated insulin bolus determination step, the bolus calculator (or bolus calculation method) can include a correction term within the bolus calculator which takes into account the body-worn sensor information. The correction term may be a factor applied to the first bolus calculated and/or a bolus shift value to add or subtract, respectively, to the first bolus calculated. The correction term will depend on the body parameter sensed by the additional sensor (different body parameters would call for the application of different correction terms). The relationship between the originally calculated bolus and the re-calculated bolus may in some embodiments be linear. In an embodiment, the re-calculated insulin bolus could for example be calculated using an algorithm as follows:

$$B2 = a_n * B1 \pm b_n$$

where B2 is the re-calculated insulin bolus;

B1 is the standard bolus calculated initially;

$a_n$ is the correction factor related to body parameter n; and $b_n$ is the bolus shift related to body parameter n.

In embodiments where there is more than one body parameter considered for the calculation, the algorithm would include an analogous calculation in the same fashion for the additional body parameter.

The respective parameters $a_n$ and $b_n$ described above can be stored in the system's firmware and in exemplary embodiments be activated and adjusted by health care practitioners and/or the user.

In another embodiment, the re-calculated insulin bolus could be calculated in the same way as the first calculated bolus, but the carbohydrate to insulin ratio, insulin sensitivity factor, and an offset compensating the activity-based basal need could be adjusted either singly or in combination to re-calculate the bolus.

In embodiments described herein, a carbohydrate input would be optional, since carbohydrate input information is needed only for meal bolus corrections.

In use, a patient would typically test their implemented algorithm in consultation with their health care practitioner to see if it suits his or her needs. If the deviation between the B1 and B2 values is too large, it may indicate some miscalculation. Thus, typically, a patient would have the opportunity through testing to find out which calculated bolus tends to be optimal for them. It is envisioned that after some amount of testing, a patient may be more comfortable with the performance of the algorithm and decide that he or she no longer needs to decide whether to accept the B1 or B2 value, but just accept the B2 value on an ongoing basis.

In embodiments herein, a significant deviation or a significant deviation threshold can be understood to constitute a difference in calculated bolus values of 10% or greater. In particular, in one aspect, the significant deviation threshold could be set at 20%. In another aspect, the user could adjust the amount of the significant deviation threshold number to be higher or lower, provided the significant deviation threshold could only be set at a value of 10% or greater. In another embodiment, the significant deviation threshold could be a selectable threshold value using either a percentage or an absolute value in insulin units.

Typically, for risk minimization purposes, the insulin administration described here could be automatically carried out by the system. However, it is also envisioned in alternative aspects that the user could turn such an automatic insulin delivery feature off.

In the above-described method, the diabetes management application can optionally receive information about a carbohydrate content associated with a meal which is to be or was recently ingested prior to calculating the first determined insulin bolus, and the carbohydrate content information can be considered by the diabetes management application in determining the first calculated insulin bolus.

In selected embodiments, the body-worn sensor device can comprise a hearing aid and/or can comprise a smart watch or activity tracker, or alternatively, a combination of these devices.

The body parameter information could include at least one of the user's heart beat rate, internal body temperature, heart rate (pulse), respiratory rate, speed of movement or acceleration of movement. In one aspect, the user's body temperature would be measured by the body-worn sensor (e.g., in one aspect, a hearing aid such as the hearing aid 38 could be utilized which would measure the user's internal body temperature by utilizing a thermometer within the ear).

The informing step can optionally include providing an audible alert to the user by use of a hearing aid such as the hearing aid 38.

In another embodiment, a diabetes management system for a continuous glucose monitoring (CGM) device is provided herein wherein the system is configured to:

obtain glucose value information from a continuous glucose monitoring device;

use the glucose information to run a loop algorithm to calculate the amount of insulin needed to keep the user within a given glucose value range (a loop algorithm refers to the system operating in a closed-loop mode (i.e., automatic feedback with no need for user interaction) or in a semi-closed loop mode (or semi-open loop mode) (i.e., requiring user interaction to confirm instructions)), wherein the algorithm would provide generally continuous information about insulin to be infused next. (This could be considered a first bolus calculation. In a loop algorithm, it is envisioned that the bolus calculation needed in this step would be carried out using the bolus calculation methods described above.);

consider body parameter information based on at least one body-worn sensor that monitors at least one body parameter;

re-calculate the insulin bolus based on the body parameter information;

inform the user if consideration of the body parameter information leads to a conclusion that the user is running out of the given glucose value range (e.g., a target glucose value range) within a preselected period of time (Here, a significant deviation threshold from the target blood glucose range would generally constitute a difference in calculated values of 10% or greater. In particular, in one aspect, the significant deviation threshold could be set at 20%. In one aspect, the user could adjust the amount of the significant deviation threshold number to be higher or lower, provided the significant deviation threshold could only be set at a value of 10% or greater.);

await an input by the user during a preset period of time whether the body parameter information will be accepted for use by the loop algorithm; and in case of no response by the user within the preset period of time, administer the lower insulin bolus which was calculated by the loop algorithm with and without consideration of the body parameter information. The connected insulin therapy device which is part of the loop system would administer the lesser value of either the first calculated insulin bolus or the re-calculated insulin bolus. In an alternative embodiment, the system could administer the bolus first calculated (i.e., the one without consideration of body parameter information). Typically, for risk minimization purposes, the insulin administration described here could be automatically carried out by the system. However, it is also envisioned in an alternative aspect that the user could turn such an automatic insulin delivery feature off.

In this embodiment, the re-calculated insulin bolus would be computed in the same fashion as set forth above with respect to the previous embodiment.

The body-worn sensor device of this embodiment can include a hearing aid and/or a smart watch or activity tracker.

The body parameter information of this embodiment can include at least one of the user's heart beat rate, internal body temperature, respiratory rate, speed or acceleration.

The informing aspect of this embodiment can include providing an audible alert to the user by use of a hearing aid.

In general, bolus calculations carried out in the above embodiments are done in two parallel paths: path 1 is a standard or traditional bolus calculation (BC1) carried out in accordance with the prior art; and path 2 is a re-calculated computation (BC2) taking information of at least one additional body sensor into account. In selected embodiments, the two bolus calculation amounts are shown to the user.

A risk is probably established if these two paths lead to different (correction or meal) bolus values. This is where the above-mentioned significant deviation comes into play. Only in the event where there is a deviation above a preset threshold (the significant deviation amount) is there an impact on the diabetes management system which would require attention by the user.

In one embodiment, if the user does not react within a given timeframe, the diabetes management system will automatically choose the lower calculated bolus to avoid a hypoglycemic condition for the user (even if the higher value would be correct). In another embodiment, the system will automatically choose the standard bolus calculation rather than the one that considers body parameter information from at least one additional body sensor.

After some time (for example, a period of weeks or months), the user supported by a health care practitioner may decide he or she is comfortable with the algorithm provided above. Together, they can fine-tune some correction factors (make adjustments) and test the algorithm under various daily conditions. At the end of this process, the optimized bolus calculation algorithm should deliver the right amount of insulin without user input (thus, the shut-off function could be utilized).

In certain embodiments, a diabetes management system can include a handheld medical device, a mobile computing device, and a diabetes management application. The handheld medical device can include a port configured to receive a test strip having a reaction site for receiving a sample of fluid from a patient, an optional real-time clock (RTC), and a blood glucose (bG) measurement system, cooperatively operable with a test strip inserted in the port, configured to measure glucose in a sample of fluid residing in the test strip and associate a first measurement time with the glucose measurement.

In selected embodiments, a computer-implemented diabetes management method is provided, comprising:

providing a diabetes management application residing on a computing device;

receiving, by the diabetes management application, a blood glucose value from a blood glucose monitoring device;

determining, by the diabetes management application, a first determined insulin bolus related to the obtained blood glucose value;

receiving, by the diabetes management application, body parameter information from at least one body-worn sensor device;

determining, by the diabetes management application, a re-calculated insulin bolus based on the body parameter information;

providing, by the diabetes management application, a notification to the user if there is a significant deviation between the amount of the first determined insulin bolus and the amount of the re-calculated insulin bolus;

setting a timer by the diabetes management application for a given timeframe;

receiving, by the diabetes management application, within the given timeframe a user input whether the calculated insulin bolus or the re-calculated insulin bolus is selected by the user for bolus administration and then administering the selected bolus amount; and determining, by the diabetes management application, whether no user input was received in the given timeframe, and if so, instructing a connected insulin therapy device to administer to the lesser value of either the first calculated insulin bolus or the re-calculated insulin bolus.

In yet another embodiment, the diabetes management application receives information about a carbohydrate content associated with a meal which is to be ingested prior to determining the first determined insulin bolus, and wherein the carbohydrate content is considered by the diabetes management application in determining the first determined insulin bolus.

In yet another embodiment, the body-worn sensor device comprises a hearing aid.

In yet another embodiment, the body-worn sensor device comprises a smart watch or activity tracker.

In yet another embodiment, the body parameter information includes at least one of the user's heart beat rate, internal body temperature, respiratory rate, speed or acceleration.

In yet another embodiment, the informing step includes providing an audible alert to the user by use of a hearing aid.

In yet another embodiment, a diabetes management method is provided and comprises the following steps:

obtaining blood glucose value information from a continuous glucose monitoring device;

using the blood glucose information to run a closed loop algorithm to calculate the amount of insulin needed to keep the user within a given blood glucose value range;

considering body parameter information based on at least one body-worn sensor that monitors at least one body parameter;

re-calculating the insulin bolus based on the body parameter information;

informing the user if consideration of the body parameter information leads to a conclusion that the user is running out of the given blood glucose value range within a preselected period of time;

awaiting an input by the user during a preset period of time whether the body parameter information will be accepted for use by the closed loop algorithm; and in case of no response by the user within the preset period of time, administering the lower insulin bolus which was calculated by the closed loop algorithm with and without consideration of the body parameter information.

In yet another embodiment, the body-worn sensor device comprises a hearing aid.

In yet another embodiment, the body-worn sensor device comprises a smart watch or activity tracker.

In yet another embodiment, the body parameter information includes at least one of the user's heart beat rate, internal body temperature, respiratory rate, speed or acceleration.

In yet another embodiment, the informing step includes providing an audible alert to the user by use of a hearing aid.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

What is claimed is:

1. A computer-implemented diabetes management method for determining an insulin bolus by a diabetes management device or component thereof comprising a processor, the method comprising:
   receiving by the processor, a glucose value;
   calculating by the processor a first calculated insulin bolus based on the received glucose value;
   receiving by the processor body parameter information from at least one body-worn sensor device;
   determining by the processor a re-calculated insulin bolus based on the body parameter information;
   notifying by a first user interface the user if there is a significant deviation between the amount of the first calculated insulin bolus and the amount of the re-calculated insulin bolus;
   receiving by the first user interface or by a second user interface within a given timeframe a user input whether the calculated insulin bolus or the re-calculated insulin bolus is selected for bolus administration;
   determining by the processor a final insulin bolus if no user input was received within the given timeframe; and
   wherein the final insulin bolus is the lesser value of either the first calculated insulin bolus or the re-calculated insulin bolus.

2. The method of claim 1 wherein in the first receiving step, the processor receives the glucose value from a glucose monitoring device.

3. The method of claim 1 further comprising administering the selected bolus amount.

4. The method of claim 1 wherein the processor receives information about a carbohydrate content associated with a meal which is to be ingested prior to determining the first calculated insulin bolus, and wherein the carbohydrate content is considered by the processor in determining the first determined insulin bolus.

5. The method of claim 1 wherein the body-worn sensor device comprises a hearing aid, a smart watch, or an activity tracker, or any combination thereof.

6. The method of claim 1 wherein the body parameter information includes at least one of the user's heart beat rate, internal body temperature, respiratory rate, speed of movement or acceleration of movement.

7. The method of claim 1 wherein the notification includes providing an audible alarm or warning to the user by use of a hearing aid, a smart watch, or an activity tracker, or any combination thereof.

8. A diabetes management system for determining an insulin amount, the system comprising a processor, wherein the processor is configured to:
   receive continuous glucose value information from a continuous glucose monitoring device;
   process the received continuous glucose value information by utilizing a loop algorithm to calculate the insulin needed to keep the user within a given glucose value range;
   receive body parameter information based on at least one body-worn sensor that monitors at least one body parameter;
   re-calculate the insulin needed to keep the user within the given glucose value range based on the body parameter information;
   provide a notification to the user if the re-calculation of insulin needed leads to a determination that the user is running out of the given glucose value range within a preselected period of time;
   receive an input by the user during a preset period of time whether the body parameter information shall be accepted for use by the loop algorithm; and
   in case of no response by the user within the preset period of time, determine that the system shall administer the lower insulin amount which was calculated by the loop algorithm with and without consideration of the body parameter information.

9. The system of claim 8 wherein the body-worn sensor device comprises a hearing aid, a smart watch, or an activity tracker, or a combination thereof.

10. The system of claim 8 wherein the body parameter information includes at least one of the user's heart beat rate, internal body temperature, respiratory rate, speed of movement or acceleration of movement.

11. The system of claim 8 wherein the processor is configured to conduct the notification by communicating to a hearing aid, a smart watch, or an activity tracker, or any combination thereof to provide an audible alert to the user.

12. A diabetes management system for determining an insulin amount, the system comprising a processor, wherein the processor is configured to:
   receive continuous glucose value information from a continuous glucose monitoring device;
   process the received continuous glucose value information by utilizing a loop algorithm to calculate the insulin needed to keep the user within a given glucose value range;
   receive body parameter information based on at least one body-worn sensor that monitors at least one body parameter;
   re-calculate the insulin needed to keep the user within the given glucose value range based on the body parameter information;
   provide a notification to the user if the re-calculation of insulin needed leads to a determination that the user is running out of the given glucose value range within a preselected period of time;
   receive an input by the user during a preset period of time whether the body parameter information shall be accepted for use by the loop algorithm; and
   in case of no response by the user within the preset period of time, determine that the system shall administer the insulin amount which was calculated by the loop algorithm without consideration of the body parameter information.

\* \* \* \* \*